US00PP10818P

United States Patent [19]

Pouw

[11] Patent Number: Plant 10,818

[45] Date of Patent: Mar. 9, 1999

[54] MINIATURE ROSE PLANT NAMED 'RUICANY'

[75] Inventor: Antonius A. Pouw, De Kwakel, Netherlands

[73] Assignee: De Ruiter's Nieuwe Rozen B.V., De Kwakel, Netherlands

[21] Appl. No.: 888,343

[22] Filed: Jul. 3, 1997

[51] Int. Cl.[6] ..... A01H 5/00

[52] U.S. Cl. ..... Plt./8.2

[58] Field of Search ..... Plt./8.2, 7.1

[56] References Cited

PUBLICATIONS

UPOV–ROM, 1998/01, Plant Variety Database, GTI Jouve Retrieval Software, citation for 'Ruicany'.

*Primary Examiner*—Howard J. Locker
*Attorney, Agent, or Firm*—C. A. Whealy

[57] ABSTRACT

A distinctive cultivar of miniature rose plant named 'Ruicany', characterized by its large golden yellow flowers; medium to dark green leaves; strong rooting habit; and excellent postproduction longevity and garden performance.

2 Drawing Sheets

The present invention relates to a new and distinct cultivar of the miniature rose class, botanically known as *Rosa hybrida,* and hereinafter referred to by the cultivar name Ruicany. The new cultivar will be marketed under the trade name Canyon Cupido.

The new cultivar is a product of a planned breeding program conducted by the inventor in Hazerswoude, The Netherlands. The objective of the breeding program was to develop compact pot rose varieties with novel and attractive flower colors and excellent postproduction longevity and garden performance. The new cultivar originated from a cross made by the inventor in 1992 of two unnamed proprietary seedlings. The cultivar Ruicany was discovered and selected by the inventor as a flowering plant within the progeny of the stated cross in a controlled environment in Hazerswoude, The Netherlands.

Asexual reproduction of the new cultivar by cuttings taken at Hazerswoude, The Netherlands, has shown that the unique features of this new miniature rose plant are stable and reproduced true to type in successive generations of asexual reproduction.

The following traits have been repeatedly observed and are determined to be the unique characteristics of 'Ruicany'. These characteristics in combination distinguish the new miniature rose plant as a new and distinct cultivar:

1. Large golden yellow flowers.
2. Medium to dark green leaves.
3. Stems without prickles.
4. Strong rooting habit.
5. Excellent postproduction longevity.
6. Excellent garden performance.

The new miniature rose plant has not been observed under all possible environmental conditions. The phenotype may vary significantly with variations in environment such as temperature and light level, without, however, any variance in genotype.

BRIEF DESCRIPTION OF PHOTOGRAPHS

The accompanying colored photographs illustrate typical specimens of the vegetative growth and flowers of the new miniature rose plant, showing the colors as true as it is reasonably possible to obtain in colored reproductions of this type.

The photograph on the first sheet comprises a side perspective view of a typical plant of the new miniature rose plant grown in Hazerswoude, The Netherlands.

The photograph on the second sheet comprises details of the new miniature rose plant. In this photograph the apex of a young shoot (1); a leaf with three leaflets (2); a leaf with five leaflets (3); a leaf with seven leaflets (4); a stem without leaves (5); a flower bud after sepals open (6); a flower bud after petals begin to unfurl (7); a flower one-half open (8); and a flower fully open (9) are shown. Flower and foliage color in these photographs may appear different from the actual colors due to light reflectance.

DETAILED BOTANICAL DESCRIPTION

The following observations, measurements, values, and comparisons describe plants grown in Hazerswoude, The Netherlands, under glass covering with average day temperatures of 20° C., average night temperatures of 16° to 18° C., and an average light level of 2,000 J/cm$^2$.

In the following description, color references are made to The Royal Horticultural Society Colour Chart except where general terms of ordinary dictionary significance are used.

Classification:

*Botanical.*—*Rose hybrida* cultivar Ruicany.

*Commercial.*—Miniature pot rose.

Parentage:

*Male or pollen parent.*—Unnamed proprietary seedling.

*Female or seed parent.*—Unnamed proprietary seedling.

Propagation:

*Type.*—Terminal or stem cuttings.

*Time to rooting.*—8 to 10 days with soil temperature of 20° C.

*Rooting habit.*—Propagates easily, roots strong and well-branched.

Plant description:

*Form.*—Rounded form, uniform, and spreading.

*Growth habit.*—Moderately vigorous, yet compact. Freely branching and dense growth. Suitable for 10-cm containers. Time to produce a finished plant in a 10-cm container 20 to 30 cm in height and 15 to 20 cm in width is generally 10 to 12 weeks depending on average temperature, light level, and cultural practices.

*Stem and lateral branches.*—Quantity of lateral branches from pinching: Typically three. Length of lateral branches: 1 to 5 cm. Diameter of lateral branches: About 1 mm. Internode length: 0.5 to 2 cm. Color: 144A.

*Foliage description.*—Leaves arranged alternately, compound with three to seven leaflets per leaf, generally symmetrical, abundant, and flat in aspect. Stipules at petiole base. Quantity of leaves: Five to eight per lateral branch. Leaflet length: 1.2 to 2.5 cm. Leaflet width: 0.8 to 1.5 cm. Shape: Ovate with acute apex and obtuse base. Margin: Serrate. Texture: Smooth. Petiole length: 0.6 to 1.8 cm. Petiole diameter: About 1 mm. Color: Young foliage, upper side: 143A with 59A at margin. Young foliage, under side: 143C with narrow 59A margin. Mature foliage, upper side: 137A. Mature foliage, under side: 137C. Petiole: 143C.

*Prickles.*—Absent.

Flower description:

*Flower type and habit.*—Large golden yellow flowers. Consistently symmetrical rosette flowers that are flat in aspect. Freely and continuously flowering. The flowers are borne singly on peduncles and arranged in clusters of up to three each. Petals persistent.

*Flowering season.*—Year-round under greenhouse conditions, optimal flowering from spring through autumn under garden conditions.

*Flower diameter.*—About 2.5 cm.

*Flower depth (height).*—About 9 mm.

*Flower longevity on plant.*—About 12 days.

*Frangrance.*—Absent.

*Flower buds.*—Shape: Ovate. Length: 1.5 to 2.5 cm. Diameter: 4 to 6 mm. Color: 143A/143B.

*Petals.*—Quantity: About 35 per flower. Typically about seven rows with five petals each. Length: About 1.2 cm. Width: 0.8 to 1 cm. Shape: Ovate with acute to pointed apex. Margin: Entire. Texture: Smooth and satiny. Color: Upper side, when opening: Light orange, 22A, towards margin; yellow, 7B, at center and base. Under side, when opening: Light orange, 22A, towards margin; yellow, 6C, at center and base. Upper side, fully opened: Mostly yellow, 7A, with narrow orange, 25A, margin. Under side, fully opened: 6A. Fade: Light salmon pink, 37C, towards margin; light yellow, 10C/10D, at center and base.

*Petaloids.*—Quantity: About 10 per flower. Arrangement: About two rows of five petaloids each. Length: About 6 mm. Width: About 1 mm. Shape: Elliptical with obtuse tip. Margin: Entire. Texture: Smooth and satiny. Color: Immature: 7A with 6A. Mature: 7A.

*Sepals.*—Quantity: Typically five per flower. Shape: Narrowly ovate with acute tip. Texture: Pubescent and leathery. Color: Upper side: 138C at base, 138A at apex. Under side: 138C at base, 138A at apex.

*Calyx.*—Length: About 3 mm. Diameter: About 4 mm. Shape: Funnel.

*Peduncles.*—Strength: High. Aspect: Erect. Length: 1 to 3 cm. Color: 144A.

*Reproductive organs.*—Stamens: Quantity: 55 to 70 per flower. Anther size: 1 to 2 mm. Anther shape: Oblong. Anther color: 6A with 23A. Pistils: Quantity: 35 to 45 per flower. Style length: About 5 mm. Style color: Almost white.

Disease resistance: Plants appear to be relatively tolerant to Powdery Mildew.

Seed production: Seed production is rarely observed.

It is claimed:

1. A new and distinct miniature rose plant named 'Ruicany', as illustrated and described.

* * * * *

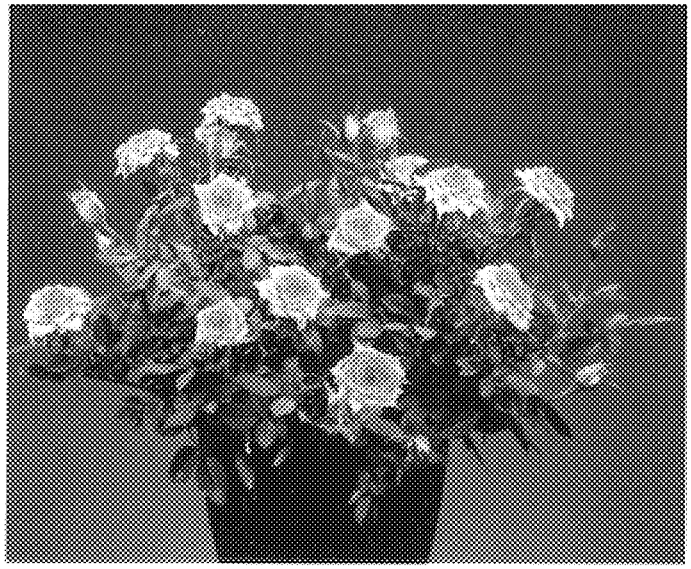

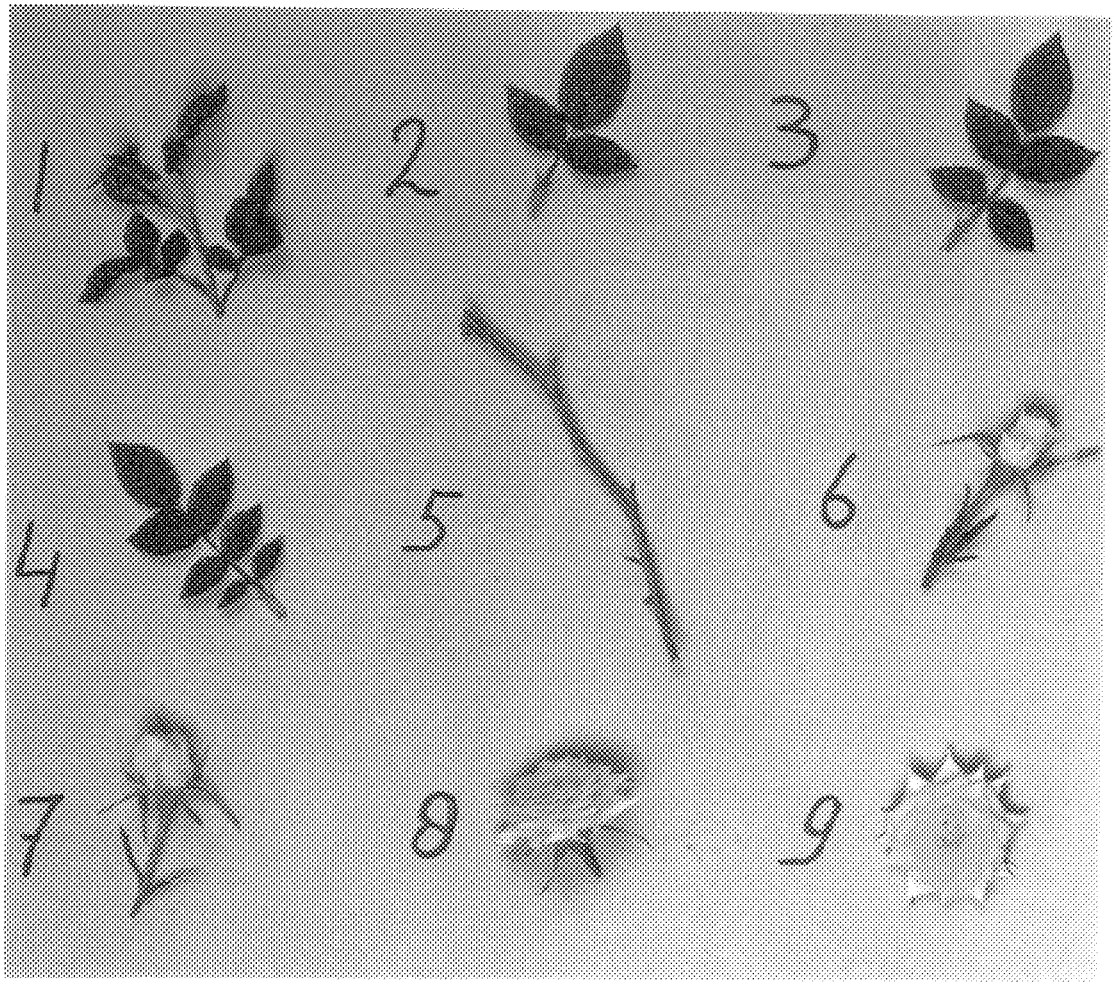
1
2
3
4
5
6
7
8
9